United States Patent [19]

Manankov

[11] 4,242,120
[45] Dec. 30, 1980

[54] METHOD FOR STIMULATING FRUCTIFICATION AND FRUIT GROWTH OF CULTIVATED PLANTS AND GIBBERELLIN-BASED PREPARATION FOR REALIZING SAME

[75] Inventor: Mikhail K. Manankov, Krymskaya, U.S.S.R.

[73] Assignee: Simferopolsky Gosudarstvenny Universitet imeni M.V., Yaltinskaya, U.S.S.R.

[21] Appl. No.: 971,630

[22] Filed: Dec. 20, 1978

[30] Foreign Application Priority Data

Feb. 23, 1978 [SU] U.S.S.R. ............................. 2595951

[51] Int. Cl.³ ............................................. A01N 43/08
[52] U.S. Cl. ..................................... 71/89; 71/DIG. 1
[58] Field of Search ............................................. 71/89

[56] References Cited
PUBLICATIONS

Weaver, Plant Growth substances in Agriculture, W. H. Freeman & Co., 1972 Muranishi, Chem. Abst. vol. 70 (1969) 19061n.

*Primary Examiner*—Catherine L. Mills
*Attorney, Agent, or Firm*—Ladas & Parry

[57] ABSTRACT

A method according to the invention is realized by local application of a stimulating agent to young one-year shoot portions adjacent to the zone of reproductive organs during the period of active fruitification.

The method is realized by using a gibberellin-based preparation containing (wt.%):

| gibberellin | from 0.5 to 90 |
|---|---|
| low-molecular carbohydrate | from 10 to 99.5 |

As the low molecular carbohydrate use is made of such substances as saccharose, glucose, fructose, maltose.

6 Claims, 3 Drawing Figures

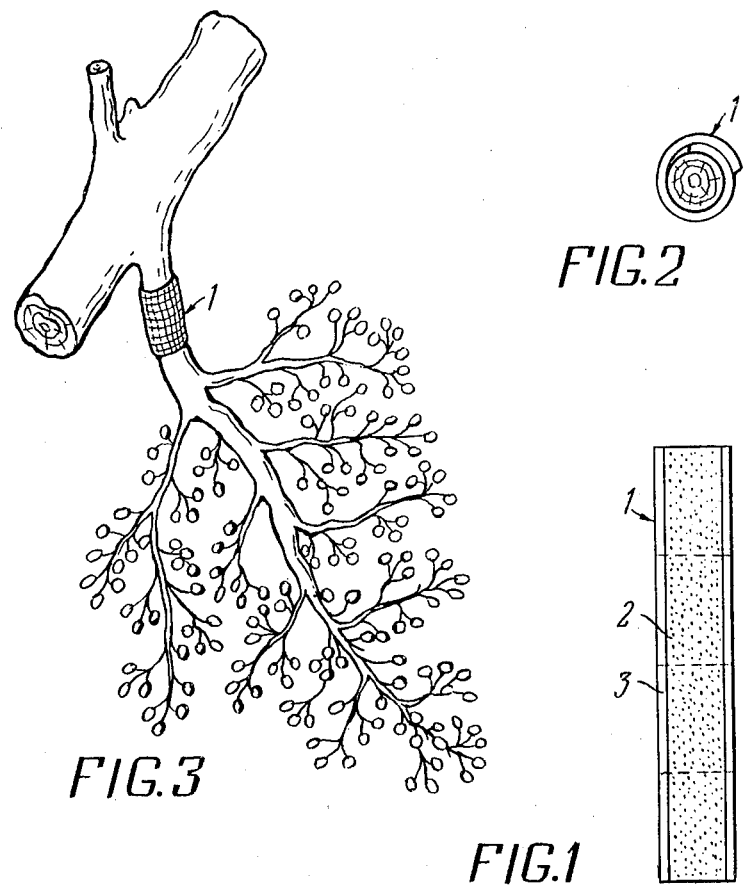

METHOD FOR STIMULATING FRUCTIFICATION AND FRUIT GROWTH OF CULTIVATED PLANTS AND GIBBERELLIN-BASED PREPARATION FOR REALIZING SAME

BACKGROUND OF THE INVENTION

1. Field of the Invention

The invention relates to processes of treating agricultural plants with gibberellin and to gibberellin-based preparations for realizing such processes.

The invention can be used to enhance the productivity of both seedless and seed-bearing varieties of grape with a tendency to parthenocarpic berry formation, of vegetable crops, such as tomatoes, eggplants, peppers, melon crops, fruit-bearing plants, such as apple-trees, pear-trees in palmette and meadow orchards, and citrus plants.

The present invention is particularly efficient in hotbed farming.

2. Description of the Prior Art

The productivity of cultivated plants is known to be increased with the use of various growth stimulators.

For example, there are known growth stimulators based on organic acids, such as 2,4,5-trichlorophenoxyacetic acid, 2,4-dichlorophenoxyacetic acid, 6-indoleacetic acid, indolebutyric acid, α-naphtylacetic acid, 2,4,5-trichlorophenoxy-α-propionic acid.

However, the preparations based on one or more of the above-cited growth stimulators did not find wide application in plant raising, since many of them showed little efficiency in stimulating fruit formation and some of them, such as 2,4-dichlorophenoxyacetic acid, adversely effect morphogenesis of treated plants.

Cytokinins, such as 6-furfurylamino purine, 6-benzylamino purine are also known to be growth stimulators. However, cytokinin-based preparations are active only in the presence of auxins, such as 6-indoleacetic acid or indolebutyric acid. The action of cytokinins on the fruictification and growth of fruit of cultivated plants has not been adequately studied and therefore these plant hormones did not find wide application in plant raising either.

Of all the known growth stimulators most widely used are gibberellins, mainly gibberellic acid. Gibberellins are obtained by microbiological synthesis from the fungi of Fusarium genus.

Commonly known methods of stimulating fructification and fruit growth of cultivated plants with the use of gibberellin (see, for example, R. J. Weaver, Plant Growth Substances in Agriculture. University of California, Davis, W. H. Freeman and Co., 1972) are based on spraying the blossom clusters with or dipping them into low-concentration liquid preparation of gibberellin.

This preparation contains from 0.002 to 0.01 wt.% of gibberellin, from 1 to 2 wt.% of ethanol, the balance being water.

Spraying of blossom clusters inevitably results in gibberellin getting on vegetative organs adjacent to the cluster and the nutrient elements are thus wasted on the growth of these organs.

Dipping of blossom clusters into gibberellin solution is therefore a more preferable technique of applying this stimulator for cultivated plant fruitification. However, solution drops trickling down from the blossom clusters may produce the same adverse effect as the spraying, and the time required for the excess gibberellin solution to flow down back into the vessel into which the blossom cluster has been dipped materially reduces the treatment efficiency.

Another adverse effect observed in spraying the blossom clusters with or dipping them into a solution is the reduction of crop quality because of the dissimilarity of the fruits formed.

When spraying technique is employed, this dissimilarity is caused by the impossibility of attaining equally uniform treatment of all the florets in a cluster with a small portion of the solution. Increasing the amount of the solution in spraying the blossom clusters dipping them into the solution does not bring about an adequate increase in the similarity of the fruits being formed, since the excess solution flows gradually down from the upper florets to the lower ones and partially to other parts of the plant.

Another disadvantage of spraying and dipping is the formation of solution drops on individual florets or other parts of the plant.

Under the conditions of intensive insolation these solution drops may cause burns of the florets and other parts of the plant whereon they fall. Treatment of blossom clusters is therefore preferably to be performed in the mornings or in the evenings, which prevents the considered method from being used over large areas.

Still another disadvantage, which is especially specific for the technique of spraying blossom clusters, is a higher consumption (as compared to physiological demand of gibberellin a part of which flows down onto the soil and is not assimilated by the plant.

It is also to be noted that in spraying and dipping the blossom clusters, gibberellin not assimilated by them remains in dry form on the fruits, which is undesirable from the sanitary-hygienic point of view.

In areas with water deficiency or in case if gibberellin solution is prepared for away from the place of its utilization, a disadvantage resides in a relatively high water requirement for the preparation of said solution, the consumption of water being from 300 to 800 l per hectare.

SUMMARY OF THE INVENTION

The principal object of the invention is to provide a method for stimulating the fruitification and growth of fruit of cultivated plants, in which method local application of a stimulating agent ensures the access thereof into fruit ovary and at the same time precludes its getting onto the blossom clusters and surface of fruits.

A further object of the invention is to provide a method suitable for local application of a stimulating agent irrespective of the time of the day.

Another object of the invention is to reduce the consumption of a gibberellin-based stimulating agent.

A further object of the invention is to enhance the productivity of cultivated fruit-bearing plants.

An additional object of the invention is to improve the uniformity of the fruits being formed.

Still another important object of the invention is to provide a gibberellin-based preparation for realizing the method and providing for a more complete assimilation of gibberellin by the plant.

An additional object of the invention is to provide a gibberellin-based preparation suitable for local application by various techniques.

These and other objects of the present invention are accomplished by that in a method for stimulating fruitification and growth of fruit of cultivated plants, comprising local application of a gibberellin-based preparation to certain parts of the plant, according to the invention, the gibberellin-based preparation is applied during the period of active fruitification to the portions of young one-year shoots adjacent to the zone of reproductive organs.

With such technique and period of local application of the stimulating agent the latter gets only into fruit ovary without acting on the adjacent vegetative organs of the plant.

The same factors practically preclude the preparation from getting onto the blossom clusters and fruits, thus reducing gibberellin consumption, improving the sanitary-hygienic properties of fruits and eliminating the possibility of floret burns on insolation.

When using the method for stimulating the fruitification and growth of grape bunches, the gibberellin-based preparation is preferably applied within a period of 5 to 30 days after the end of mass flowering of grapevine onto the grape rachis at the base thereof.

The best results in using the method under high insolation conditions for treating tomatoes, eggplants, pepper, black currants according to the invention are attained when the gibberellin-based preparation is applied within 1 to 15 days after the end of mass flowering of these plants to the stem portion adjacent to the zone of reproductive organs.

In using the method under low insolation conditions for stimulating fruit growth in tomatoes, the gibberellin-based preparation is preferably applied within 1 to 15 days after the end of mass flowering.

In using the method for treating apple trees, pear trees, eggplants, pepper, and citrus plants, the gibberellin-based preparation is preferably applied within 1 to 15 days after the end of mass flowering of these plants.

Local application of a powdery gibberellin-based preparation onto young shoot portions adjacent to the zone of reproductive organs is preferably accomplished by sticking an adhesive tape with the preparation sprayed thereupon.

The above-mentioned and other objects are also accomplished by that the preparation for realizing the method of the invention, comprising a gibberellin growth stimulator, according to the invention, additionally contains a low-molecular carbohydrate as a gibberellin transport activator for transferring thereof from the zone of its local application to the reproductive organs, said ingredients being taken in the following proportions (wt.%):

| gibberellin | from 0.5 to 90 |
|---|---|
| low-molecular carbohydrate | from 10 to 99.5 |

When used in combination with a low-molecular carbohydrate, gibberellin is better assimilated by the plant and is more intensively transported along the capillaries to the fruit ovaries.

From the economic point of view, the most preferable low-molecular carbohydrate activator is sucrose which also imparts adhesive properties to the preparation.

It is most convenient to perform local application of the preparation when it additionally contains ethanol and water as solvents, the ingredients being taken in the following weight percentage ratio:

| gibberellin | from 0.5 to 30 |
|---|---|
| low-molecular carbohydrate | from 10 to 40 |
| ethanol | from 5 to 80 |
| water | the balance |

It will be apparent that sucrose as a low-molecular carbohydrate used in the preparation may be substituted by such substances as glucose, fructose, maltose, etc., but this is economically unjustified and such formulations will not be considered hereinbelow.

BRIEF DESCRIPTION OF THE DRAWINGS

The essence of the present invention is hereinafter explained by reference to specific embodiments thereof and accompanying drawings, in which:

FIG. 1 shows an adhesive tape with the preparation sprayed thereon for the local application thereof, according to the invention;

FIG. 2 shows the adhesive tape applied;

FIG. 3 shows a bunch of grapes with an adhesive tape bearing the preparation applied to the grape rachis.

DETAILED DESCRIPTION OF THE INVENTION

EXAMPLE 1

According to the invention, fructification and fruit growth stimulation was performed for the "Kishmish black" variety of trape cultivated on nonirrigated dark brown soils at an average annual temperature of $+14°$ C. and annual precipitation from 400 to 450 mm.

The stimulation was performed on fruit-bearing 10-year old plants, the growing bush maintained fan-like, consisting of 4 to 6 sleeves arranged, on a vertical flat trellis. Feeding area of one bush was 3.75 $m^2$.

Gibberellin obtained by microbiological synthesis from a commercial strain of Fusarium moniliforme and containing, according to the Manufacturer's data 82% of an active substance (as gibberellic acid) was used as the fructification and fruit growth stimulator.

Said stimulator is a fine dispersed white powder with a creamy shade, readily soluble in ethanol at a temperature of from 10° to 25° C. and poorly soluble in water.

Prior to formulating working preparations, the activity of said stimulator was determined by following a conventional procedure comprising:

dissolving gibberellin in ethanol in a proportion of 100 mg gibberellin to 12 ml of ethanol with further dilution of the alcoholic gibberellin solution with water to a concentration of 5 mg/l;

preparing standard solutions of gibberellic acid with concentrations of 1,2,3,5,10 mg per liter of water;

soaking seeds of stunt pea in water for 12 hours and germinating them at a temperature of $+26°$ C. for 48 hours;

putting germinated stunt pea seeds into small cups containing each 4 ml of the above solutions with a respective concentration (5 seeds into each cup);

growing said germinated seeds at a temperature of $+26°$ C. for 7 days;

determining the sprout length in each cup and estimating gibberellin activity (as compared with gibberellic acid) by comparing an average length of said sprouts grown on the gibberellin preparation with an average length of sprouts grown on the gibberellic acid preparation.

The activity of the gibberellin used as determined by the described procedure was 82%.

The controlled gibberellin was used to prepare a control working preparation and a working preparation according to the invention.

The control working preparation had the following chemical composition (wt.%):

| | |
|---|---|
| gibberellin | 0.01 |
| ethanol | 1.00 |
| water | the balance |

This preparation was obtained by dissolving 1 g of gibberellin in 5 ml of ethanol and subsequently diluting the resultant alcoholic gibberellin solution with water.

The working preparation according to the invention had the following chemical composition (wt.%):

| | |
|---|---|
| gibberellin | 0.5 |
| low-molecular carbohydrate (sucrose) | 99.5 |

To obtain this preparation, the calculated amount of gibberellin was first dissolved in ethanol, the proportions being 1 g of gibberellin per 5 ml of ethanol, whereupon the resultant alcoholic solution was used to wet the calculated amount of sucrose powder. This mixture was thoroughly stired, dried at a temperature of 50° to 60° C. and the resultant dry gibberellin-sucrose mixture was ground to powder.

The control working preparation was applied to grape vine by two methods.

The first method was to spray the grape vine blossom clusters during the period of mass flowering. The second one was to dip the grape vine blossom clusters during the period of mass flowering into a vessel with the control working solution of the preparation for 3 to 4 seconds.

The working preparation was applied with the aid of an adhesive tape and a strip of an adhesive plaster 1 shown in FIG. 1 of the drawings was used as such a tape.

Powdered working preparation 2 is sprayed on the middle portion of the tape; portions 3 adjoining the side edges being free from the preparation retain the tackiness. The adhesive tape is wound around the grape rachis at the base thereof as is clearly seen in FIGS. 2 and 3.

The working preparation according to the invention was applied 5 days after the end of mass flowering.

The gathered crop was studied to determine the uniformity of grape berry development in bunches, average bunch weight, average weight of 100 grape berries, average number of grape berries in a bunch, and sugar content and acidity of grape sap.

To assess the uniformity of berry development in a bunch, the berries were classified according to their size into large, medium and small ones and a relative percentage of each class was determined.

To assess an average bunch weight, 100 typical grape bunches taken from a test sample were weighed, and an average bunch weight was calculated.

To assess an average weight of 100 berries, 1000 berries selected from 50 typical bunches were weighed.

To assess an average number of berries in a bunch, the number of berries in 25 typical bunches was calculated, and an average number of berries in one bunch was determined.

To assess sugar content, the density of grape berry cell sap was determined using a refractometer, with subsequent calculation of the total percentage of sugars from known relationships.

To assess acidity, grape berry cell sap was titrated with a 0.1 M aqueous solution of sodium hydrate in the presence of phenolphtalein indicator, with subsequent calculation of the total acid content from a conventional relation.

The results of comparative studies are given in the table:

| | | Values | | |
|---|---|---|---|---|
| | Characteristics and units of | Control working preparation | | Working preparation according to the |
| Nos. | measurement | spraying | dipping | invention |
| 1. | Uniformity of berry development in bunches as percentage of large, medium and small berries | 20:42:38 | 10:58:32 | 30:50:20 |
| 2. | Average bunch weight (kg) | 0.316 | 0.321 | 0.340 |
| 3. | Average weight of 100 berries (kg) | 0.176 | 0.172 | 0.194 |
| 4. | Average number of berries in a bunch | 170 | 178 | 166 |
| 5. | Sugar content (%) | 19.4 | 18.8 | 20.0 |
| 6. | Acidity (%) | 6.4 | 6.6 | 6.4 |

EXAMPLE 2

According to the invention the stimulation of fructification and fruit growth was performed for "Kishmish black" variety of grape cultivated under the same conditions as described in Example 1.

Physico-chemical properties of gibberellin used as the stimulator were the same as those described in Example 1.

The controlled gibberellin was used to prepare a control working preparation having the qualitative and quantitative composition similar to that described in Example 1, and a working preparation according to the invention.

The control working preparation was obtained by following the same procedure as described in Example 1.

The working preparation according to the invention had the following chemical composition (wt.%):

| | |
|---|---|
| gibberellin | 20 |
| low-molecular carbohydrate (surose) | 80 |

The procedure used to obtain the working preparation was identical to that described in Example 1.

The control working preparation was applied to grape vine as described in Example 1.

The working preparation was applied to the grape rachis at the base thereof 10 days after the end of mass flowering. The powdered working preparation was sprayed on an adhesive plaster tape (5 mg of the preparation per $cm^2$ of the adhesive plaster tape), and the preparation was applied as described in Example 1.

The gathered crop was studied to determine the uniformity of berry development in bunches, average bunch weight, average weight of 100 berries, average number of berries in a bunch, sugar content and acidity of grape sap.

The above characteristics were assessed as described in Example 1.

The results of comparative studies are given in the table

|     | Characteristics and units of | Values | | |
|-----|---|---|---|---|
|     | | Control working preparation | | Working preparation and method according to the invention |
| No. | measurements | spraying | dipping | |
| 1. | Uniformity of berry development in bunches as percentage of large, medium and small berries | 20:42:38 | 10:58:32 | 90:8:2 |
| 2. | Average bunch weight (kg) | 0.316 | 0.321 | 0.523 |
| 3. | Average weight of 100 berries (kg) | 0.176 | 0.172 | 0.333 |
| 4. | Average number of berries in a bunch | 170 | 178 | 150 |
| 5. | Sugar content (%) | 19.4 | 18.8 | 19.6 |
| 6. | Acidity (%) | 6.4 | 6.6 | 5.9 |

EXAMPLE 3

According to the invention the stimulation of fructification and fruit growth was performed for "Kishmish black" variety of grape cultivated under the same conditions as described in Example 1.

Physico-chemical properties of gibberellin used as the stimulator were similar to those described in Example 1.

The controlled gibberellin was used to prepare a control working preparation having the qualitative and quantitative composition similar to that described in Example 1, and a working preparation according to the invention.

The control working preparation was obtained by the procedure identical to that described in Example 1.

The working preparation according to the invention had the following chemical composition (wt. %):

| gibberellin | 90 |
|---|---|
| low-molecular carbohydrate (sucrose) | 10 |

The procedure used to obtain the working preparation was identical to that described in Example 1.

The control working preparation was applied to grapevine as described in Example 1.

The working preparation was applied to the grape rachis at the base thereof 30 days after the end of mass flowering. The powdered working preparation was sprayed on an adhesive plaster tape (5 mg of preparation per cm² of the adhesive plaster tape), and the preparation was applied as described in Example 1.

The gathered crop was studied to determine the uniformity of berry development in bunches, average bunch weight, average weight of 100 berries, average number of berries in a bunch, and sugar content and acidity of grape sap.

The above-stated characteristics were assessed as described in Example 1.

The results of comparative studies are given in the table.

|     | Characteristics and units of | Values | | |
|-----|---|---|---|---|
|     | | Control working preparation | | Working preparation and method according to the invention |
| No. | measurement | spraying | dipping | |
| 1. | Uniformity of berry development in bunches as percentage of large, medium and small berries | 20:42:38 | 10:58:32 | 68:20:12 |
| 2. | Average bunch weight (kg) | 0.316 | 0.321 | 0.490 |
| 3. | Average weight of 100 berries (kg) | 0.176 | 0.172 | 0.299 |
| 4. | Average number of berries in a bunch | 170 | 178 | 158 |
| 5. | Sugar content (%) | 19.4 | 18.8 | 19.2 |
| 6. | Acidity (%) | 6.4 | 6.6 | 6.3 |

EXAMPLE 4

According to the invention, the stimulation of fructification and fruit growth was performed for "Kishmish white" variety of grape cultivated under the same conditions as described in Example 1.

Physico-chemical properties of gibberellin used as the stimulator were similar to those described in Example 1.

The controlled gibberellin was used to prepare a control working preparation having the qualitative and quantitative composition similar to that described in Example 1, and a working preparation according to the invention.

The control working preparation was obtained by the procedure identical to that described in Example 1.

The working preparation according to the invention had the following chemical composition (wt. %):

| gibberellin | 5 |
|---|---|
| low-molecular carbohydrate (sucrose) | 95 |

The procedure used to obtain the working preparation was identical to that described in Example 1.

The control working preparation was applied to grapevine as described in Example 1.

The working preparation was applied to the grape rachis at the base thereof 10 days after the end of mass flowering. The powdered working preparation was sprayed on an adhesive plaster tape (5 mg of the preparation per cm² of the adhesive plaster tape), and the preparation was applied as described in Example 1.

The gathered crop was studied to determine the uniformity of berry development in bunches, average bunch weight, average weight of 100 berries, average number of berries in a bunch, and sugar content and acidity of grape sap.

The above-stated characteristics were assessed as described in Example 1.

The results of comparative studies are given in the table.

| Order | Characteristics and units of measurement | Values | | |
|---|---|---|---|---|
| | | Control working preparation | | Working preparation and method according to the invention |
| | | spraying | dipping | |
| 1. | Uniformity of berry development in bunches as percentage of large, medium and small berries | 11:42:17 | 19:61:20 | 70:21:9 |
| 2. | Average bunch weight (kg) | 0.306 | 0.320 | 0.468 |
| 3. | Average weight of 100 berries (kg) | 0.129 | 0.128 | 0.211 |
| 4. | Average number of berries in a bunch | 224 | 236 | 208 |
| 5. | Sugar content (%) | 19.6 | 19.3 | 19.3 |
| 6. | Acidity (%) | 6.8 | 6.7 | 6.7 |

EXAMPLE 5

According to the invention, the stimulation of fructification and growth was performed for "Kishmish white" variety of grape cultivated under the same conditions as described in Example 1.

Physico-chemical properties of gibberellin used as the stimulator were similar to those described in Example 1.

The controlled gibberellin was used to prepare a control working preparation having the qualitative and quantitative composition similar to that described in Example 1, and a working preparation according to the invention.

The control working preparation was obtained by the procedure identical to that described in Example 1.

The working preparation according to the invention had the following composition (wt. %):

| | |
|---|---|
| gibberellin | 60 |
| low-molecular carbohydrate (sucrose) | 40 |

The procedure used to obtain the working preparation was identical to that described in Example 1.

The control working preparation was applied to grape-vine as described in Example 1.

The working preparation was applied to the grape rachis at the base thereof 20 days after the end of mass flowering. The powdered working preparation was sprayed on an adhesive plaster tape (5 mg of the preparation per cm$^2$ of the adhesive plaster tape), and the preparation was applied as described in Example 1.

The gathered crop was studied to determine the uniformity of berry development in bunches, average bunch weight, average weight of 100 berries, average number of berries in a bunch, and sugar content and acidity of grape sap.

The above-stated characteristics were assessed as described in Example 1.

The results of comparative studies are given in the table.

| No. | Characteristics and units of measurement | Values | | |
|---|---|---|---|---|
| | | Control working preparation | | Working preparation and method according to the invention |
| | | spraying | dipping | |
| 1. | Uniformity of berry development in bunches as percentage of large, medium and small berries | 11:42:7 | 19:61:20 | 65:30:5 |
| 2. | Average bunch weight (kg) | 0.306 | 0.320 | 0.503 |
| 3. | Average weight of 100 berries (kg) | 0.129 | 0.128 | 0.243 |
| 4. | Average number of berries in a bunch | 224 | 236 | 195 |
| 5. | Sugar content (%) | 19.6 | 19.3 | 19.0 |
| 6. | Acidity (%) | 6,8 | 6,7 | 6.9 |

EXAMPLE 6

According to the invention, the stimulation of fructification and fruit growth was performed for "Korinka black" variety of grape cultivated under the same conditions as described in Example 1.

Physico-chemical properties of gibberellin used as the stimulator were similar to those described in Example 1.

The controlled gibberellin was used to prepare a control working preparation having the qualitative and quantitative composition similar to that described in Example 1, and a working preparation according to the invention.

The control working preparation was obtained by the procedure identical to that described in Example 1.

The working preparation according to the invention had the following composition (wt.%):

| | |
|---|---|
| gibberellin | 1 |
| low-molecular carbohydrate (sucrose) | 99 |

The procedure used to obtain the working preparation was identical to that described in Example 1.

The control working preparation was applied to grape vine as described in Example 1.

The working preparation was applied to the grape rachis at the base thereof 5 days after the end of mass flowering. The powdered working preparation was sprayed on an adhesive plaster tape (5 mg of the preparation per cm$^2$ of the adhesive plaster tape), and the preparation was applied as described in Example 1.

The gathered crop was studied to determine the uniformity of berry development in bunches, average bunch weight, average weight of 100 berries, average number of berries in a bunch, and sugar content and acidity of grape sap.

The above-specified characteristics were assessed as described in Example 1.

The results of comparative studies are given in the table.

| No. | Characteristics and units of measurement | Values | | |
|---|---|---|---|---|
| | | Control working preparation | | Working preparation and method according to the invention |
| | | spraying | dipping | |
| 1. | Uniformity of berry development in bunches as percentage of large, medium and small berries | 22:40:38 | 15:60:25 | 29:66:15 |
| 2. | Average bunch weight (kg) | 0.186 | 0.200 | 0.256 |
| 3. | Average weight of 100 berries (kg) | 0.059 | 0.059 | 0.085 |
| 4. | Average number of berries in a bunch | 296 | 320 | 286 |
| 5. | Sugar content (%) | 23.0 | 22.4 | 23.0 |
| 6. | Acidity (%) | 6.3 | 5.9 | 6.4 |

EXAMPLE 7

According to the invention, the stimulation of fructification and fruitgrowth was performed for "Korinka black" variety of grape cultivated under the same conditions as described in Example 1.

Physico-chemical properties of gibberellin used as the stimulator were similar to those described in Example 1.

The controlled gibberellin was used to prepare a control working preparation hwaving the qualitative and quantitative composition similar to that described in Example 1, and a working preparation according to the invention.

The control working preparation was obtained by the procedure identical to that described in Example 1.

The working preparation according to the invention had the following composition (wt.%):

| gibberellin | 10 |
|---|---|
| low-molecular carbohydrate (sucrose) | 90 |

The procedure used to obtain the working preparation was identical to that described in Example 1.

The control working preparation was applied to grape vine as described in Example 1.

The working preparation was applied to the grape rachis at the base thereof 10 days after the end of mass flowering. The powdered working preparation was sprayed on an adhesive plaster tape (5 mg of the preparation per cm² of the adhesive plaster tape), and the preparation was applied as described in Example 1.

The gathered crop was studied to determine the uniformity of berry development in bunches, average, bunch weight, average weight of 100 berries, average number of berries in a bunch, and sugar content of acidity of trape sap.

The above characteristics were assessed as described in Example 1.

The results of comparative studies are given in the table.

| Nos. | Characteristics and units of measurement | Values | | |
|---|---|---|---|---|
| | | Control working preparation | | Working preparation and method according to the invention |
| | | spraying | dipping | |
| 1. | Uniformity of berry development in bunches as a percentage of large, medium and small berries | 22:40:38 | 15:60:25 | 60:29:11 |
| 2. | Average bunch weight (kg) | 0.186 | 0.200 | 0.386 |
| 3. | Average weight of 100 berries (kg) | 0.059 | 0.059 | 0.143 |
| 4. | Average number of berries in a bunch | 296 | 320 | 252 |
| 5. | Sugar content (%) | 23.0 | 22.4 | 22.0 |
| 6. | Acidity (%) | 6.3 | 5.9 | 5.9 |

EXAMPLE 8

According to the invention, the stimulation of fructification and fruitgrowth was performed for "Kishmish black" variety of grape cultivated under the same conditions as described in Example 1.

The controlled gibberellin was used to prepare a control working preparation having the qualitative and quantitative composition similar to that described in Example 1, and a working preparation according to the invention.

The control working preparation was obtained by the procedure identical to that described in Example 1.

The working preparation according to the invention had the following composition (wt.%):

| gibberellin | 0.5 |
|---|---|
| low-molecular carbohydrate (sucrose) | 30 |
| ethanol | 5 |
| water | the balance |

To obtain the above working preparation, the calculated amount of gibberellin was dissolved in the calculated amount of ethanol at a temperature of 70° to 90° C., and the calculated amount of sucrose was dissolved at the same temperature in the calculated amount of water. Then the prepared solutions were combined and agitated until a homogeneous solution was formed.

The control working preparation was applied to grape vine as described in Example 1.

The working preparation was applied to the grape rachis at the base thereof 5 days after the end of mass flowering.

The working preparation was applied to grape-vine by pressing a porolon (an elastic poroplast based on plasticized polyvinylchloride) sponge, presoaked in the above working preparation, around the above-mentioned part of the grape-vine.

The gathered crop was studied to determine the uniformity of berry development in a bunch, average bunch weight, average weight of 100 berries, average number of berries in a bunch, and sugar content and acidity of grape sap.

The above-stated characteristics were assessed as described in Example 1.

The results of comparative studies are given in the table.

| Nos. | Characteristics and units of measurement | Values | | |
|---|---|---|---|---|
| | | Control working preparation | | Working preparation and method according to the invention |
| | | spraying | dipping | |
| 1. | Uniformity of berry development in bunches as a percentage of large, medium and small berries | 20:42:38 | 10:58:32 | 25:50:17 |
| 2. | Average bunch weight (kg) | 0.316 | 0.321 | 0.341 |
| 3. | Average weight of 100 berries (kg) | 0.176 | 0.172 | 0.193 |
| 4. | Average number of berries in a bunch | 170 | 178 | 166 |
| 5. | Sugar content (%) | 19.4 | 18.8 | 21.0 |
| 6. | Acidity (%) | 6.4 | 6.6 | 6.3 |

EXAMPLE 9

According to the invention, the stimulation of fructification and growth of fruit was performed for "Kishmish black" variety of grape cultivated under the same conditions as described in Example 1.

Physico-chemical properties of gibberellin used as the stimulator were similar to those described in Example 1.

The controlled gibberellin was used to prepare a control working preparation having the qualitative and quantitative composition similar to that described in Example 1, and a working preparation according to the invention.

The control working preparation was obtained by the procedure identical to that described in Example 1.

The working preparation according to the invention had the following composition (wt.%):

| | |
|---|---|
| gibberellin | 2 |
| low-molecular carbohydrate (sucrose) | 40 |
| ethanol | 20 |
| water | the balance |

To obtain the above working preparation, the calculated amount of gibberellin was dissolved in the calculated amount of ethanol at a temperature of 70° to 90° C., and the calculated amount of saccharose was dissolved at the same temperature in the calculated amount of water. Then the resultant solutions were combined and agitated until a homogeneous solution was formed.

The control working preparation was applied to grape-vine as described in Example 1.

The working preparation was applied to the grape rachis at the base thereof 10 days after the end of mass flowering.

The working preparation was applied to grape vine by pressing a porolon sponge, presoaked in the above working preparation, around the above-mentioned part of the grave vine.

The gathered crop was studied to determine the uniformity of berry development in a bunch, average bunch weight of 100 berries, average number of berries in a bunch, and sugar content and acidity of grape sap.

The above-stated characteristics were assessed as described in Example 1.

The results of comparative studies are given in the table.

| Order | Characteristics and units of measurement | Values | | |
|---|---|---|---|---|
| | | Control working preparation | | Working preparation and method according to the invention |
| | | spraying | dipping | |
| 1. | Uniformity of berry development in bunches as a percentage of large, medium and small berries | 20:42:38 | 10:58:32 | 70:23:7 |
| 2. | Average bunch weight (kg) | 0.316 | 0.321 | 0.436 |
| 3. | Average weight of 100 berries (kg) | 0.176 | 0.172 | 0.279 |
| 4. | Average number of berries in a bunch | 170 | 178 | 147 |
| 5. | Sugar content (%) | 19.4 | 18.8 | 19.0 |
| 6. | Acidity (%) | 6.4 | 6.6 | 5.9 |

EXAMPLE 10

According to the invention, the stimulation of fructification and fruitgrowth was performed for "Kishmish black" variety of grape cultivated under the same conditions as described in Example 1.

Physico-chemical properties of gibberellin used as the stimulator were similar to those described in Example 1.

The controlled gibberellin was used to prepare a control working preparation having the qualitative and quantitative composition similar to that described in Example 1, and a working preparation according to the invention.

The control working preparation was obtained by the procedure identical to that described in Example 1.

The working preparation according to the invention had the following composition (wt.%):

| | |
|---|---|
| gibberellin | 30 |
| low-molecular carbohydrate (sucrose) | 10 |
| ethanol | 50 |
| water | the balance |

To obtain the above working preparation, the calculated amount of gibberellin was dissolved in the calculated amount of ethanol at a temperature of 70° to 90° C., and the calculated amount of saccharose was dissolved at the same temperature in the calculated amount of water. Then the resulting solutions were combined and agitated until a homogeneous solution was formed.

The control working preparation was applied to grape-vine as described in Example 1.

The working preparation was applied to the grape rachis at the base thereof 20 days after the end of mass flowering.

The working preparation was applied to grape vine by pressing a porolon sponge, presoaked in the above working preparation, around the above-mentioned part of the grape vine.

The gathered crop was studied to determine the uniformity of berry development in a bunch, average bunch weight, average weight of 100 berries, average number of berries in a bunch, and sugar content and acidity of grape sap.

The above stated characteristics were assessed as described in Example 1.

The results of comparative studies are given in the table.

| Nos. | Characteristics and units of measurement | Values | | |
|---|---|---|---|---|
| | | Control working preparation | | Working preparation and method according to the invention |
| | | spraying | dipping | |
| 1. | Uniformity of berry development in bunches as percentage of large, medium and small berries | 10:42:38 | 10:58:32 | 74:18:4 |
| 2. | Average bunch weight (kg) | 0.316 | 0.321 | 0.500 |
| 3. | Average weight of 100 berries (kg) | 0.176 | 0.172 | 0.324 |
| 4. | Average number of berries in a bunch | 170 | 178 | 148 |
| 5. | Sugar content (%) | 19.4 | 18.8 | 19.0 |
| 6. | Acidity (%) | 6.4 | 6.6 | 6.2 |

EXAMPLE 11

According to the invention, the stimulation of fructification and fruit growth was performed for "Kishmish white" variety of grape cultivated under the same conditions as described in Example 1.

Physico-chemical properties of gibberellin used as the stimulator were similar to those described in Example 1.

The controlled gibberellin was used to prepare a control working preparation having the qualitative and quantitative composition similar to that described in Example 1, and a working preparation according to the invention.

The control working preparation was obtained by the procedure identical to that described in Example 1.

The working preparation according to the invention had the following composition (wt.%):

| gibberellin | 2 |
|---|---|
| low-molecular carbohydrate (sucrose) | 30 |
| ethanol | 10 |
| water | the balance |

The procedure used to obtain the working preparation was identical to that described in Example 8.

The control working preparation was applied to grape vine as described in Example 1.

The working preparation was applied to the grape rachis at the base thereof 10 days after the end of mass flowering. The application was carried out as described in Example 8.

The gathered crop was studied to determine the uniformity of berry development in a bunch, average bunch weight, average weight of 100 berries, average number of berries in a bunch, and sugar content and acidity of grape sap.

The above-stated characteristics were assessed as described in Example 1.

The results of comparative studies are given in the table.

| Nos. | Characteristics and units of measurement | Values | | |
|---|---|---|---|---|
| | | Control working preparation | | Working preparation and method according to the invention |
| | | spraying | dipping | |
| 1. | Uniformity of berry development in bunches as percentage of large, medium and small berries | 11:42:17 | 19:61:20 | 73:24:3 |
| 2. | Average bunch weight (kg) | 0.306 | 0.320 | 0.434 |
| 3. | Average weight of 100 berries (kg) | 0.129 | 0.128 | 0.180 |
| 4. | Average number of berries in a bunch | 224 | 236 | 229 |
| 5. | Sugar content (%) | 19.6 | 19.3 | 19.0 |
| 6. | Acidity (%) | 6.8 | 6.7 | 6.4 |

EXAMPLE 12

According to the invention, the stimulation of fructification and fruitgrwoth was performed for "Kishmish white" variety of grape cultivated under the same conditions as described in Example 1.

Physico-chemical properties of gibberellin used as the stimulator were similar to those described in Example 1.

The controlled gibberellin was used to prepare a control working preparation having qualitative and quantitative composition similar to that described in Example 1, and a working preparation according to the invention.

The control working preparation was obtained by the procedure identical to that described in Example 1.

The working preparation according to the invention had the following composition (wt.%):

| gibberellin | 5 |
|---|---|
| low-molecular carbohydrate (sucrose) | 20 |
| ethanol | 20 |
| water | the balance |

The procedure used to obtain the working preparation was identical to that described in Example 8.

The control working preparation was applied to grape vine as described in Example 8.

The control working preparation was applied to grape vine as described in Example 1.

The working preparation was applied to the grape rachis at the base thereof 5 days after the end of mass flowering. The application was carried out as described in Example 8.

The gathered crop was studied to determine the uniformity of berry development in a bunch, average bunch weight, average weight of 100 berries, average number of berries in a bunch, and sugar content and acidity of grape sap.

The above-stated characteristics were assessed as described in Example 1.

The results of comparative studies are given in the table.

| Order | Characteristics and units of measurement | Control working preparation spraying | Control working preparation dipping | Working preparation and method according to the invention |
|---|---|---|---|---|
| 1. | Uniformity of berry development in bunches as percentage of large, medium and small berries | 11:42:17 | 19:61:20 | 78:15:7 |
| 2. | Average bunch weight (kg) | 0.306 | 0.320 | 0.496 |
| 3. | Average weight of 100 berries (kg) | 0.129 | 0.128 | 0.204 |
| 4. | Average number of berries in a bunch | 224 | 236 | 228 |
| 5. | Sugar content (%) | 19.6 | 19.3 | 19.4 |
| 6. | Acidity (%) | 6.8 | 6.7 | 6.7 |

EXAMPLE 13

According to the invention, the stimulation of fructification and fruitgrowth was performed for "Kishmish white" variety of grape cultivated under the same conditions as described in Example 1.

Physico-chemical properties of gibberellin used as the stimulator were similar to those described in Example 1.

The controlled gibberellin was used to prepare a control working preparation having the qualitative and quantitative composition similar to that described in Example 1, and a working preparation according to the invention.

The control working preparation was obtained by the procedure identical to that described in Example 1.

The working preparation according to the invention had the following composition (wt.%):

| | |
|---|---|
| gibberellin | 15 |
| low-molecular carbohydrate (sucrose) | 20 |
| ethanol | 30 |
| water | the balance |

The procedure used to obtain the working preparation was identical to that described in Example 8.

The control working preparation was applied to grape vine as described in Example 1.

The working preparation was applied to the grape rachis at the base thereof 30 days after the end of mass flowering. The application was carried out as described in Example 8.

The gathered crop was studied to determine the uniformity of berry development in a bunch, average bunch weight, average weight of 100 berries, average number of berries in a bunch, and sugar content and acidity of grape sap.

The above stated characteristics were assessed as described in Example 1.

The results of comparative studies are given in the table.

| Nos. | Characteristics and units of measurement | Control working preparation spraying | Control working preparation dipping | Working preparation and method according to the invention |
|---|---|---|---|---|
| 1. | Uniformity of berry development in bunches as percentage of large, medium and small berries | 11:42:17 | 19:61:20 | 54:31:15 |
| 2. | Average bunch weight (kg) | 0.306 | 0.320 | 0.441 |
| 3. | Average weight of 100 berries (kg) | 0.129 | 0.128 | 0.205 |
| 4. | Average number of berries in a bunch | 224 | 236 | 195 |
| 5. | Sugar content (%) | 19.4 | 19.3 | 18.5 |
| 6. | Acidity (%) | 6.8 | 6.7 | 6.7 |

EXAMPLE 14

According to the invention, the stimulation of fructification and fruitgrowth was performed for "Korinka black" variety of grape cultivated under the same conditions as described in Example 1.

Physico-chemical properties of gibberellin used as the stimulator were similar to those described in Example 1.

The controlled gibberellin was used to prepare a control working preparation having the qualitative and quantitative composition similar to that described in Example 1 and a working preparation according to the invention.

The control working preparation was obtained by the procedure identical to that described in Example 1.

The working preparation according to the invention had the following composition (wt.%):

| | |
|---|---|
| gibberellin | 10 |
| low-molecular carbohydrate (sucrose) | 20 |
| ethanol | 40 |
| water | the balance |

The procedure used to obtain the working preparation was identical to that described in Example 8.

The control working preparation was applied to grape vine as described in Example 1.

The working preparation was applied to the grape rachis at the base thereof 20 days after the end of mass flowering. The application was carried out as described in Example 8.

The gathered crop was studied to determine the uniformity of berry development in a bunch, average bunch weight, average weight of 100 berries, average number of berries in a bunch, and sugar content and acidity of grape sap.

The above-stated characteristic were assessed as described in Example 1.

The results of comparative studies are given in the table.

| Nos. | Characteristics and units of measurement | Values | | | | Nos. | Characteristics and units of measurement | Values | | |
|---|---|---|---|---|---|---|---|---|---|---|
| | | Control working preparation | | Working preparation and method according to the Invention | | | | Control working preparation | | Working preparation and method according to the invention |
| | | spraying | dipping | | | | | spraying | dipping | |
| 1. | Uniformity of berry development in bunches as a percentage of large, medium and small berries | 22:40:38 | 15:60:25 | 67:20:13 | | 1. | Uniformity of berry development in bunches as a percentage of large, medium and small berries | 22:40:38 | 15:60:25 | 18:56:16 |
| 2. | Average bunch weight (kg) | 0.186 | 0.200 | 0.376 | | 2. | Average bunch weight (kg) | 0.186 | 0.200 | 0.286 |
| 3. | Average weight of 100 berries (kg) | 0.059 | 0.059 | 0.139 | | 3. | Average weight of 100 berries (kg) | 0.059 | 0.059 | 0.091 |
| 4. | Average number of berries in a bunch | 296 | 320 | 258 | | 4. | Average number of berries in a bunch | 296 | 320 | 298 |
| 5. | Sugar content (%) | 23.0 | 22.4 | 23.0 | | 5. | Sugar content (%) | 23.0 | 22.4 | 23.0 |
| 6. | Acidity (%) | 6.3 | 5.9 | 6.1 | | 6. | Acidity (%) | 6.3 | 5.9 | 6.4 |

EXAMPLE 15

According to the invention the stimulation of fructification and fruitgrowth was performed for "Korinka black" variety of grape cultivated under the same conditions as described in Example 1.

Physico-chemical properties of gibberellin used as stimulator were similar to those described in Example 1.

The controlled gibberellin was used to prepare a control working preparation having the qualitative and quantitative composition similar to that described in Example 1, and a working preparation according to the invention.

The control working preparation was obtained by the procedure identical to that described in Example 1.

The working preparatinn according to the invention had the following composition (wt.%):

| | |
|---|---|
| gibberellin | 2 |
| low-molecular carbohydrate (sucrose) | 10 |
| ethanol | 80 |
| water | the balance |

The procedure used to obtain the working preparation was identical to that described in Example 8.

The control working preparation was applied to grape vine as described in Example 1.

The working preparation was applied to the grape rachis at the base thereof 5 days after the end of mass flowering. The application was carried out as described in Example 8.

The gathered crop was studied to determine the uniformity of berry development in a bunch, average bunch weight, average weight of 100 berries, average number of berries in a bunch, and sugar content and acidity of grape sap.

The above characteristics were assessed as described in Example 1.

The results of comparative studies are given in the table.

EXAMPLE 16

According to the invention, the stimulation of fructification and fruitgrowth was performed for "Kishmish black" variety of grape cultivated under the same conditions as described in Example 1.

Physico-chemical properties of gibberellin used as the stimulator were similar to those described in Example 1.

The controlled gibberellin was used to prepare a control working preparation having the qualitative and quantitative composition similar to that described in Example 1, and a working preparation having a widely known and commonly used qualitative and quantitative composition.

The control working preparation was obtained by the procedure identical to that described in Example 1.

The working preparation had the following chemical composition (wt.%):

| | |
|---|---|
| gibberellin | 1 |
| water | the balance |

The procedure used to obtain the working preparation was identical to that described in Example 1 for obtaining the control working preparation.

The control working preparation was applied to grape vine as described in Example 1.

The working preparation was applied to the grape rachis at the base thereof 20 days after the end of mass flowering. The application was carried out as described in Example 8.

The gathered crop was studied to determine the uniformity of berry development in bunches, average bunch weight, average weight of 100 berries, average number of berries in a bunch, and sugar content and acidity of grape sap.

The above-stated characteristics were assessed as described in Example 1.

The results of comparative studies are given in the table.

| Nos. | Characteristics and units of measurement | Values Control working preparation | | Working preparation and method according to the invention |
|---|---|---|---|---|
| | | spraying | dipping | |
| 1. | Uniformity of berry development in bunches as a percentage of large, medium and small berries | 10:42:38 | 10:58:32 | 26:51:23 |
| 2. | Average bunch weight (kg) | 0.316 | 0.321 | 0.344 |
| 3. | Average weight of 100 berries (kg) | 0.176 | 0.172 | 0.181 |
| 4. | Average number of berries in a bunch | 170 | 178 | 183 |
| 5. | Sugar content (%) | 19.4 | 18.8 | 19.1 |
| 6. | Acidity (%) | 6.4 | 6.6 | 6.4 |

EXAMPLE 17

According to the invention, the stimulation of fructification and fruitgrowth was performed for "Revermoon" variety of tomatoes (*Solanum lycopersicum*) cultivated under hothouse conditions. Feeding area of one bush was 0.25 m². Gibberellin with physico-chemical properties similar to those indicated in Example 1 was used as the fruitification and fruitgrowth stimulator.

The controlled gibberellin was used to obtain a control preparation having the following qualitative and quantitative composition (wt.%):

| gibberellin | 0.005 |
|---|---|
| water | 99.995 |

The same controlled gibberellin was used to obtain a working preparation according to the invention with the following proportions of the ingredients (wt.%):

| gibberellin | 10 |
|---|---|
| low-molecular carbohydrate (sucrose) | 90 |

The procedure used to obtain the working preparation was identical to that described in Example 1.

The working preparation was applied with the aid of an adhesive plaster to the raceme at the base thereof 7 days after the end of mass flowering.

The gathered crop was studied to determine the uniformity of fruit development in racemes, the percentage of fruit-setting in a raceme, average fruit weight, and the percentage of deformed fruits.

The results of comparative studies are given in the table.

| Nos. | Characteristics and units of measurement | Values Control working preparation and methods | | Working preparation and method according to the invention |
|---|---|---|---|---|
| | | spraying | dipping | |
| 1. | Uniformity of fruit development in racemes as a percentage of large, medium and small fruits | 20:35:45 | 9:30:61 | 60:36:4 |
| 2. | Average fruit weight (g) | 53.3 | 43.6 | 102 |
| 3. | Percentage of fruit-setting in a raceme | 56.3 | 61.2 | 70 |
| 4. | Percentage of deformed fruits | 58.3 | 53.8 | 5.1 |

EXAMPLE 18

According to the invention, the stimulation of fructification and fruit growth was performed for "Revermoon" variety of tomatoes (*Solanum lycopersicum*) cultivated under hothouse conditions. Feeding area of one bush was 0.25 m². Gibberellin with physico-chemical properties similar to those indicated in Example 1 was used as the fruitification and fruit growth stimulator.

The controlled gibberellin was used to obtain a control preparation having the following qualitative and quantitative composition (wt.%):

| gibberellin | 0.005 |
|---|---|
| water | 99.995 |

The same controlled gibberellin was used to obtain a working preparatin according to the invention with the following proportions of the igredients (wt.%):

| gibberellin | 2 |
|---|---|
| low-molecular carbohydrate (sucrose) | 40 |
| ethanol | 20 |
| water | 38 |

The procedure used to obtain the working preparation was identical to that described in Example 1.

The working preparation was applied with a porolon sponge to the raceme at the base thereof 15 days after the end of mass flowering.

The gathered crop was studied to determine the uniformity of fruit development in racemes, percentage of fruit-setting in a raceme, average fruit weight, and percentage of deformed fruits.

The results of comparative studies are given in the table.

| Nos. | Characteristics and units of measurement | Values Control working preparation and methods | | Working preparation and method according to the invention |
|---|---|---|---|---|
| | | spraying | dipping | |
| 1. | Uniformity of fruit development in racemes as percentage of large, medium and small fruits | 20:35:45 | 9:30:61 | 30:56:14 |
| 2. | Average fruit weight (g) | 53.3 | 43.6 | 98.6 |
| 3. | Percentage of fruit-setting in a raceme | 56.3 | 61.2 | 65.1 |

-continued

| | | Values | |
|---|---|---|---|
| | | Control working preparation and methods | Working preparation and method according to the invention |
| Nos. | Characteristics and units of measurement | spraying | dipping | |
| 4. | Percentage of deformed fruits | 58.3 | 53.8 | 8.7 |

EXAMPLE 19

According to the invention, the stimulation of fructification and fruit growth was performed for "Revermoon" variety of tomatoes (*Solanum lycopersicum*) cultivated under hothouse conditions. Feeding area of one bush was 0.25 m². Gibberellin with physico-chemical properties similar to those obtained in Example 1 was used as the fruitification and fruit growth stimulator.

The controlled gibberellin was used to obtain a control preparation having the following qualitative and quantitative composition (wt.%):

| gibberellin | 0.005 |
|---|---|
| water | 99.995 |

The same controlled gibberellin was used to obtain a working preparation according to the invention with the following proportions of the ingredients (wt.%):

| gibberellin | 5 |
|---|---|
| low-molecular carbohydrate (sucrose) | 20 |
| ethanol | 20 |
| water | 55 |

The procedure used to obtain the working preparation was identical to that described in Example 1.

The working preparation was applied with a porolon sponge to the raceme at the base thereof 7 days after the end of mass flowering.

The gathered crop was studied to determine the uniformity of fruit development in racemes, percenrage of fruit-setting in a raceme, average fruit weight, and percentage of deformed fruits.

The results of comparative studies are given in the table.

| | | Values | | |
|---|---|---|---|---|
| | | Control working preparation and methods | | Working preparation and method according to the invention |
| Nos. | Characteristics and units of measurement | spraying | dipping | |
| 1. | Uniformity of fruit development in racemes as percentage of large, medium and small fruits | 20:35:45 | 9:30:61 | 36:52:12 |
| 2. | Average fruit weight (g) | 53.3 | 43.6 | 94.3 |
| 3. | Percentage of fruit-setting in a raceme | 56.3 | 61.2 | 78.6 |
| 4. | Percentage of deformed fruits | 58.3 | 53.8 | 20 |

EXAMPLE 20

According to the invention, the stimulation of fructification and fruit growth was performed for "Mayak" variety of tomatoes (*Solanum lycopersicum*) cultivated in open irrigated ground. Feeding area of one bush was 0.25 m². Gibberellin with physicochemical properties similar to those indicated in Example 1 was used as the fruitification and fruit growth stimulator.

The controlled gibberellin was used to obtain a control working preparation and a preparation according to the invention.

The control working preparation had the following composition (wt.%):

| gibberellin | 0.005 |
|---|---|
| water | 99.995 |

The working preparation according to the invention had the following composition (wt.%):

| gibberellin | 10 |
|---|---|
| low-molecular carbohydrate (sucrose) | 20 |
| ethanol | 40 |
| water | 30 |

The working preparation was applied with the aid of a sponge onto the main rachis of the raceme at the base thereof 7 days after the end of mass flowering.

Control plants were treated by spraying with the control working preparation.

The gathered crop was studied to determine the uniformity of fruit development in racemes, percentage of fruit-setting in a raceme, average fruit weight, and percentage of deformed fruits.

The results of comparative studies are given in the table.

| | | Values | | |
|---|---|---|---|---|
| | | Control working preparation and methods | | Working preparation and method according to the invention |
| Nos. | Characteristics and units of measurement | spraying | dipping | |
| 1. | Uniformity of fruit development in racemes as percentage of large, medium and small fruits | 31:29:40 | — | 68:25:7 |
| 2. | Average fruit weight (g) | 80 | | 126 |
| 3. | Percentage of fruit-setting in a raceme | 67 | — | 86 |
| 4. | Percentage of deformed fruits | 43 | — | 8 |

EXAMPLE 21

According to the invention, the stimulation of fructification and fruit growth was performed for "Mayak" variety of tomatoes (*Solanum lycopersicum*) cultivated in open irrigated ground. Feeding area of one bush was 0.25 m². Gibberellin with physico-chemical properties similar to those indicated in Example 1 was used as the fruitification and fruit growth stimulator.

The controlled gibberellin was used to obtain a control working preparation and a preparation according to the invention.

The control working preparation had the following composition (wt.%):

| | |
|---|---|
| gibberellin | 0.005 |
| water | 99.995 |

The working preparation according to the invention had the following composition (wt.%):

| | |
|---|---|
| gibberellin | 20 |
| low-molecular carbohydrate (sucrose) | 80 |

The working preparation was applied with the aid of an adhesive plaster to a one-year stem near reproductive organs 7 days after the end of mass flowering. Control plants were treated by spraying with the control working preparation.

The gathered crop was studied to determine the uniformity of fruit development in racemes, percentage of fruit-setting in a raceme, average fruit weight, and percentage of deformed fruits.

The results of comparative studies are given in the table.

| | | Values | | |
|---|---|---|---|---|
| | | Control working preparation and methods | | Working preparation and method according to the invention |
| Nos. | Characteristics and units of measurement | spraying | dipping | |
| 1. | Uniformity of fruit development in racemes as percentage of large, medium and small fruits | 31:29:40 | — | 68:21:11 |
| 2. | Average fruit weight (g) | 80 | — | 121 |
| 3. | Percentage of fruit-setting in a raceme | 67 | — | 81 |
| 4. | Percentage of deformed fruits | 43 | — | 6 |

EXAMPLE 22

According to the invention, the stimulation of fructification and fruit growth was performed for "Maikopsky" variety of eggplants (*Solanum melangena*) cultivated in open irrigated ground. Feeding area of one bush was 0.42 m$^2$. Gibberellin with physico-chemical properties similar to those indicated in Example 1 was used as the stimulator.

The controlled gibberellin was used to obtain a control working preparation and a working preparation according to the invention.

The control working preparation had the following chemical composition (wt. %):

| | |
|---|---|
| gibberellin | 0.005 |
| water | the balance |

The control working preparation was obtained by the procedure identical to that described in Example 1.

The working preparation according to the invention had the following chemical composition (wt.%):

| | |
|---|---|
| gibberellin | 20 |
| low-molecular carbohydrate (sucrose) | 80 |

The procedure used to obtain the working preparation was identical to that described in Example 1.

The working preparation was applied to the stem portion adjacent to eggplant reproductive organs 10 days after the end of mass flowering. The application was carried out as described in Example 1.

The gathered crop was studied to determine an average fruit weight, the percentage of fruit-setting, and the uniformity of fruit development in a bush as the percentage of large, medium and small fruits.

The results of comparative studies are given in the table.

| | | Values | | |
|---|---|---|---|---|
| | | Control working preparation | | Working preparation and method according to the invention |
| Nos. | Characteristics and units of measurement | spraying | dipping | |
| 1. | Average fruit weight (g) | 0.231 | — | 0.284 |
| 2. | Percentage of fruit-setting | 61 | — | 73.4 |
| 3. | Uniformity of fruit development as percentage of large. medium and small fruits | 10:41:49 | — | 25:61:14 |

EXAMPLE 23

According to the invention, the stimulation of fructification and growth was performed for "Maikopsky" variety of eggplants (*Solanum melangena*) cultivated in open irrigated ground. Feeding area of one bush was 0.42 m$^2$. Gibberellin with physico-chemical properties similar to those indicated in Example 1 was used as the stimulator.

The controlled gibberellin was used to obtain a control working preparation and a working preparation according to the invention.

The control working preparation had the following chemical composition (wt.%):

| | |
|---|---|
| gibberellin | 0.005 |
| water | the balance |

The control working preparation was obtained by the procedure identical to that described in Example 1.

The working preparation according to the invention had the following chemical composition (wt.%):

| | |
|---|---|
| gibberellin | 2 |
| low-molecular carbohydrate (sucrose) | 40 |
| ethanol | 20 |
| water | the balance |

The working preparation was obtained by the procedure identical to that described in Example 8.

The working preparation was applied to the pedicels of the plant 15 days after the end of mass flowering.

The application was carried out as described in Example 8.

The crop gathered was studied to determine an average fruit weight, the percentage of fruit-setting, and the uniformity of fruit development in a bush as the percantage of large, medium and small fruits.

The results of comparative studies are given in the table.

| Nos. | Characteristics and units of measurement | Values | | |
|---|---|---|---|---|
| | | Control working preparation | | Working preparation and method according to the invention |
| | | spraying | dipping | |
| 1. | Average fruit weight (g) | 0.231 | — | 0.305 |
| 2. | Percentage of fruit-setting | 61 | — | 78.3 |
| 3. | Uniformity of fruit development as percentage of large, medium and small fruits | 10:41:49 | — | 36:51:13 |

EXAMPLE 24

According to the invention, the stimulation of fructification and fruit growth was performed for "Nikitsky white" variety of pepper (*Capsicum annum* L) cultivated in open irrigated ground. Feeding area of one bush was 0.42 m$^2$.

Gibberellin with physico-chemical properties similar to those indicated in Example 1 was used as the stimulator.

The controlled gibberellin was used to obtain a control working preparation and a working preparation according to the invention.

The control working preparation had the following chemical composition (wt.%):

| gibberellin | 0.005 |
|---|---|
| water | the balance |

The control working preparation was obtained by the procedure identical to that described in Example 1.

The working preparation according to the invention had the following chemical composition (wt.%):

| gibberellin | 20 |
|---|---|
| low-molecular carbohydrate (sucrose) | 80 |

The procedure used to obtain the working preparation was identical to that described in Example 1.

The working preparation was applied to the stem portion adjacent to pepper re-productive organs 8 days after the end of mass flowering. The application was carried out as described in Example 1.

The gathered crop was studied to determine an average fruit weight, the percentage of fruit-setting, and the uniformity of fruit development in a bush as the percentage of large, medium and small fruits.

The results of comparative studies are given in the table.

| Nos. | Characteristics and units of measurement | Values | | |
|---|---|---|---|---|
| | | Control working preparation | | Working preparation and method according to the invention |
| | | spraying | dipping | |
| 1. | Average fruit weight (g) | 0.014 | — | 0.021 |
| 2. | Percentage of fruit-setting | 73 | — | 92.3 |
| 3. | Uniformity of fruit development as percentage of large, medium and small fruits | 31:40:29 | — | 56:39:5 |

EXAMPLE 25

According to the invention, the stimulation of fructification and fruit growth was performed for "Nikitsky white" variety of pepper (*Capsicum annum* L) cultivated in open irrigated ground. Feeding area of one bush was 0.42 m$^2$.

Gibberellin with physico-chemical properties similar to those indicated in Example 1 was used as the stimulator.

The controlled gibberellin was used to obtain a control working preparation and a working preparation according to the invention.

The control working preparation had the following chemical composition (wt.%):

| gibberellin | 0.005 |
|---|---|
| water | the balance |

The control working preparation was obtained by the procedure identical to that described in Example 1.

The working preparation according to the invention had the following chemical composition (wt.%):

| gibberellin | 2 |
|---|---|
| low-molecular carbohydrate (sucrose) | 30 |
| ethanol | 10 |
| water | the balance |

The procedure used to obtain the working preparation was identical to that described in Example 8.

The working preparation was applied to the pedicels of the plant 5 days after the end of mass flowering. The method by which the working preparation was applied is identical to that described in Example 8.

The gathered crop was studied to determine an average fruit weight, the percentage of fruit-setting, and the uniformity of fruit development in a bush as a relative percentage of large, medium and small fruits.

The results of comparative studies are given in the table:

| Nos. | Characteristics and units of measurement | Values | | |
|---|---|---|---|---|
| | | Control working preparation | | Working preparation and method according to the invention |
| | | spraying | dipping | |
| 1. | Average fruit weight (g) | 0.014 | — | 0.026 |
| 2. | Percentage of fruit-setting | 73 | — | 96.2 |
| 3. | Uniformity of fruit development as percentage of large, medium and small fruits | 31:40:29 | — | 70:21:9 |

EXAMPLE 26

According to the invention, the stimulation of fructification and fruit growth was performed for fruits of appletrees grown in open irrigated ground. Feeding area of one tree was 48 m². Soil and climate conditions were similar to those described in Example 1. The plants were irrigated twice during the vegetation period: in spring and in summer. Gibberellin with physico-chemical properties similar to those indicated in Example 1 was used as the stimulator.

The controlled gibberellin was used to obtain a control working preparation and a working preparation according to the invention. The control working preparation contained 50 mg of gibberellin per 1 of water. The composition of the working preparation according to the invention was as follows (wt.%):

| | |
|---|---|
| gibberellin | 5 |
| low-molecular carbohydrate (sucrose) | 20 |
| ethanol | 20 |
| water | the balance |

The control working preparation was applied to control plants by spraying the flowers.

The working preparation was applied according to the invention with the aid of a porolon sponge 10 days after the end of mss flowering.

The gathered crop was studied to determine an average fruit weight, the percentage of developed fruits, and the uniformity of fruit development.

The results of comparative studies are given in the table.

| Nos. | Characteristics and units of measurement | Values | | |
|---|---|---|---|---|
| | | Control working preparation | | Working preparation and method according to the invention |
| | | spraying | dipping | |
| 1. | Average fruit weight (kg) | 0.033 | — | 0.048 |
| 2. | Percentage of developed fruits | 18.6 | — | 29.6 |
| 3. | Uniformity of fruit development as percentage of large, medium and small fruits | 17:60:23 | — | 41:50:9 |

EXAMPLE 27

According to the invention, the stimulation of fructification and fruit growth was performed for black currants cultivated in open irrigated ground. Feeding area of one bush was 0.6 m². Soil and climate conditions were similar to those described in Example 1. The plants were irrigated twice during the vegetation period: in spring and in summer. Gibberellin with physico-chemical properties similar to those indicated in Example 1 was used as the stimulator.

The controlled gibberellin was used to obtain a control working preparation and a preparation according to the invention. The control working preparation contained 50 mg of gibberellin per 1 of water. The composition of the working preparation according to the invention was as follows (wt.%):

| | |
|---|---|
| gibberellin | 20 |
| low-molecular carbohydrate (sucrose) | 80 |

The control working preparation was applied to control plants by spraying the inflorescence.

The working preparation was applied according to the invention with the aid of an adhesive plaster onto a one-year stem near the reproductive organs 1 day after the end of mass flowering.

The gathered crop was studied to determine an average weight of 100 berries, the percentage of developed fruits and the uniformity of fruit development.

The results of comparative studies are given in the table.

| Nos. | Characteristics and units of measurement | Values | | |
|---|---|---|---|---|
| | | Control working preparation | | Working preparation and method according to the invention |
| | | spraying | dipping | |
| 1. | Average weight of 100 berries (kg) | 0.089 | — | 0.168 |
| 2. | Percentage of developed fruits | 41.1 | — | 61.3 |
| 3. | Uniformity of fruit development as percentage of large, medium and small berries | 10:40:50 | — | 36:45:19 |

EXAMPLE 28

According to the invention, the stimulation of fructification and fruit growth was performed for fruits of pear trees grown in open irrigated ground. Feeding area of one tree was 36 m². Soil and climate conditions were similar to those described in Example 1. The plants were irrigated twice during the vegetation period: in spring and in summer. Gibberellin with physico-chemical properties similar to those described in Example 1 was used as the stimulator.

The controlled gibberellin was used to obtain a control working preparation and a preparation according to the invention. The control working preparation contained 50 mg of gibberellin per 1 of water. The composition of the working preparation in accordance with the invention was as follows (wt.%):

| | |
|---|---|
| gibberellin | 20 |
| low-molecular carbohydrate (sucrose) | 80 |

The control working preparation was applied to control plants by spraying the flowers.

The working preparation was applied according to the invention with the aid of an adhesive plaster to the fruitstalk 7 days after the end of mass flowering.

The gathered crop was studied to determine an average fruit weight, the percentage of developed fruits, and the uniformity of fruit development.

The results of comparative stuides are given in the table.

| | | Values | | |
|---|---|---|---|---|
| | | Control working preparation | | Working preparation and method according to the |
| Nos. | Charateristics and units of measurements | spraying | dipping | invention |
| 1. | Average fruit weight (kg) | 0.029 | — | 0.040 |
| 2. | Percentage of developed fruits | 19.8 | — | 27.1 |
| 3. | Uniformity of fruit development as percentage of large, medium and small fruits | 30:27:43 | — | 47:31:22 |

EXAMPLE 29

According to the invention, the stimulation of fruit formation and growth was performed for "Novo-Gruzinsky" variety of lemon cultivated under glasshouse conditions. Feeding are of one tree was 9 m².

Gibberellin with physico-chemical properties similar to those indicated in Example 1 was used as the stimulator.

The controlled gibberellin was used to obtain a control working preparation and a working preparation according to the invention.

The control working preparation had the following chemical composition (wt.%):

| | |
|---|---|
| gibberellin | 0.005 |
| water | the balance |

The procedure used to obtain the control working preparation was identical to that described in Example 1.

The working preparation according to the invention had the following chemical composition (wt.%):

| | |
|---|---|
| gibberellin | 20 |
| low-molecular carbohydrate (sucrose) | 80 |

The procedure used to obtain the working preparation was identical to that described in Example 1.

The working preparation was applied to the fruitstalk of the plant 10 days after the end of mass flowering. The method by which the working preparation was applied is identical to that described in Example 1.

The gathered crop was studied to determine an average fruit weight, the percentage of fruit-setting, and the uniformity of fruit development on a tree.

The results of comparative studies are given in the table.

| | | Values | | |
|---|---|---|---|---|
| | | Control working preparation | | Working preparation and method according to the |
| Order | Characteristics and units of measurement | spraying | dipping | invention |
| 1. | Average fruit weight (kg) | 0.051 | — | 0.068 |
| 2. | Percentage of fruit-setting | 18.1 | — | 27.3 |
| 3. | Uniformity of fruit development on a tree as percentage of large, medium and small fruits | 10:41:49 | — | 25:48:27 |

It will be apparent to those skilled in the art that the invention has been described hereinabove with reference to certain particular embodiments thereof and that various changes and modifications may be resorted to without departing from the true spirit and scope of the invention as defined in the claims.

We claim:

1. A method for stimulating the fruitification and fruit growth of cultivated plants, comprising locally applying an effective amount of a preparation containing gibberellin and low molecular weight carbohydrate to individual parts of plants adjacent to reproductive organs during the period of active fruit formation.

2. A method as claimed in claim 1, wherein in stimulating grape, the gibberellin- and low molecular weight carbohydrate-containing preparation is applied to the grape rachis at the base thereof within a period of 5 to 30 days after the end of mass flowering of grape vine.

3. A method as claimed in claim 1, wherein in stimulating tomatoes, eggplants, pepper, black currants, the gibberellin- and low molecular weight carbohydrate-containing preparation is applied to the stem portion adjacent to the zone of reproductive organs.

4. A method as claimed in claim 1, wherein in stimulating tomatoes, the gibberellin- and low molecular weight carbohydrate-containing preparation is applied to the main rachis at the base thereof within a period of 1 to 15 days after the end of mass flowering of tomatoes.

5. A method as claimed in claim 1, wherein in stimulating apple- trees, pear trees, eggplants, pepper, citrus plants, the gibberellin- and low molecular weight carbohydrate-containing preparation is applied to the fruitstalk within a period of 1 to 15 days after the end of mass flowering of the plants.

6. A method as claimed in claim 1, wherein the local application of the gibberellin- and low molecular weight carbohydrate-contining preparation to young one-year shoot portions adjacent to the zone of reproductive organs is accomplished by sticking to said shoot portions an adhesive tape with the preparation sprayed thereon.

* * * * *